United States Patent [19]

Stapel et al.

[11] Patent Number: 4,618,605

[45] Date of Patent: Oct. 21, 1986

[54] PROCESS FOR THE PRODUCTION OF β-ELEMONIC ACID AND PHARMACEUTICAL PREPARATIONS CONTAINING SAID ACID

[76] Inventors: Günter Stapel, Münstereifeler St. 30, 5000 Köln 41; Karl-Heinz Gober, Archimedesstr. 38, 5000 Köln 80; Sigurd Leyck, Am Quechenhauf 21, 5024 Pulheim 2; Helmut Wetzig, Paulstr. 46, 5024 Pulheim-Sinnersdorf; Christian Birkner, Grubenbecherstr., 5000 Köln 30; Kurt Kesselring, Villenweg 49, 5024 Erfstadt-Köttingen; Bruno Christ, Peter Franzen-Str. 44, 5000 Köln 3; Klaus Steiner, Gartenstr. 18, 5024 Pulheim-Stommeln; Friedhelm Schröder, An der Maar 10, 5024 Pulheim 2, all of Fed. Rep. of Germany

[21] Appl. No.: 660,957

[22] Filed: Oct. 15, 1984

[30] Foreign Application Priority Data

Oct. 13, 1983 [DE] Fed. Rep. of Germany ....... 3337229

[51] Int. Cl.$^4$ .............................................. A61K 31/56
[52] U.S. Cl. .................................. 514/177; 260/397.1
[58] Field of Search ...................... 260/397.1; 514/182

[56] References Cited

PUBLICATIONS

"Steroids" (1959), by Fieser et al, pp. 397–398.
Fieser and Fieser, "Steroide", Verlag Chemie (1961), pp. 436–437.
Halsall, et al., *J. of Chem. Soc.*, "The Chemistry of the Triterpenes and Related Compounds . . . Some Aspects of the Chemistry of the Elemi Acids", pp. 4139–4148 (1953).
*Hagers Handbuch der Pharmazeutischen Praxis*, vol. 4, pp. 765–755 (1973).

*Primary Examiner*—Elbert L. Roberts
*Attorney, Agent, or Firm*—Keil & Weinkauf

[57] ABSTRACT

Disclosed is a process for the production of β-elemonic acid from an alcoholic solution of gum elemi by recovering a crude mixture of elemi acids containing β-elemonic acid, $\Delta^7\alpha$-elemonic acid and $\Delta^8\alpha$-elemolic acid by the use of a basic ion exchanger, isomerizing the $\Delta^7\alpha$-elemolic acid to $\Delta^8\alpha$-elemolic acid in a chlorinated hydrocarbon by use of a mineral acid, oxidizing the $\Delta^8\alpha$-elemolic acid to yield additional β-elemonic acid and separating and purifying the total resulting β-elemonic acid from the acid mixture. Also disclosed are pharmaceutical preparations for the treatment of inflammatory conditions containing β-elemonic acid as the active ingredient.

4 Claims, No Drawings

PROCESS FOR THE PRODUCTION OF β-ELEMONIC ACID AND PHARMACEUTICAL PREPARATIONS CONTAINING SAID ACID

The present invention relates to a process for the recovery and production of β-elemonic acid and to pharmaceutical preparations for human and veterinary therapy which contain β-elemonic acid as active component, especially for the treatment of inflammatory conditions.

β-Elemonic acid (13α, 14β, 17α, 20S,-3-Oxo-lanosta-8,24-dien-21-carboxylic acid)

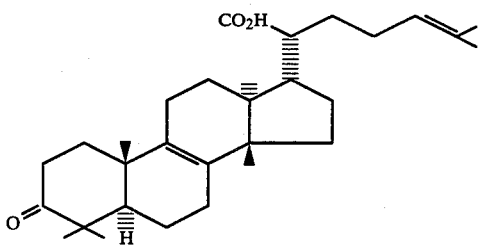

is known triterpene, which occurs in the so-called gum elemi. Gum elemi is obtained from various Burseraceae, especially those of the genus Canaricum (Berger, Vol. 6, pp. 97-99; Hagers Handbuch der Pharm. Praxis, Vol. IV, pp. 765-766). Gum elemi contains about 20-30% etheric oils, about 20-25% amyrines, 5-6% elemi acids and various sesquiterpene alcohols and other triterpene acids. Gum elemi was used in folk medicine for covering septic wounds or was used as a plaster base for better adhesion. The gum is also useful in industry for the preparation of lacquers and varnishes and for finishing felt fabrics. In order to elucidate the structure of the triterpene acids from gum elemi, L. Ruzicka and H. Haeusermann, for example, isolated the individual substances (Helv. Chim. Acta, 1942, 25, 439-57). β-Elemonic acid, which occurs in gum elemi to the extent of only about 2%, has not yet been used in therapy, nor have there yet been any known pharmaceutical investigations.

It is an object of the invention to provide a particularly advantageous process for the recovery and production of β-elemonic acid from plants or plant resins for use in pharmaceutical preparations.

The present invention provides a process for the production of β-elemonic acid from an alcoholic solution of gum elemi which comprises recovering a crude mixture of elemi acids consisting essentially of β-elemonic acid, $\Delta^7\alpha$-elemolic acid and $\Delta^8\alpha$-elemolic acid by the use of a basic ion exchanger, isomerizing the $\Delta^7\alpha$-elemolic acid to $\Delta^8\alpha$-elemolic acid in a chlorinated hydrogen by use of a mineral acid, oxidizing the $\Delta^8$-α-elemolic acid of the crude acid mixture to yield further β-elemonic acid and separating the total resulting β-elemonic acid from the crude acid mixture. Preferably, the separated β-elemonic acid is purified by chromatography on silica gel.

The invention also provides pharmaceutical preparations which contain β-elemonic acid as the active principle. Thus, it has been surprisingly found that the purified β-elemonic acid possesses a strong anti-inflammatory effect. β-Elemonic acid is thus particularly suitable for therapy and treatment of rheumatic illnesses, e.g. arthroses or chronic polyarthritis, in which it is distinguished by being very well tolerated.

According to processes known up to the present for the isolation of β-elemonic acid from gum elemi, especially Manila elemi, the gum is dissolved in an organic solvent immiscible with water, e.g. dialkyl ethers, alkylcarboxylic esters, hydrocarbons, halogenated hydrocarbons or aromatics such as toluene, and then intensively mixed with an aqueous alkaline solution, especially 0.5N soldium hydroxide. The aqueous alkaline phase is separated, acidified to a pH of 3 with 20-30% hydrochloric acid and stirring, and then shaken out with an organic solvent, e.g. toluene, and the organic phase is dried. After evaporation of the solvent there is obtained a mixture of elemi acids (L. Ruzicka, J. R. Hosking and A. Wick, Helv. Chim. Acta 14 (1931), 811-820). From this mixture the β-elemonic acid is converted to a hydrazone by reaction with Girard-T-Reagent, and separated from the other elemi acids by shaking out with water. After being liberated by acidification, the β-elemonic acid can be extracted and isolated pure (L. Ruzicka and H. Haeusermann, Helv. Chim. Acta 25 (1942) 439-57).

Manila gum elemi contains on the average
- 3-5% β-elemonic acid
- 8-10% $\Delta^8\alpha$-elemolic acid
- 4-6% $\Delta^8\alpha$-elemolic acid.

According to the known methods, only the 3-5% β-elemonic acid is accessible to isolation. Further costly purification steps are necessary to convert, by oxidation, the $\Delta^8\alpha$-elemolic acid which is present in the gum into β-elemonic acid.

A process has now been discovered whereby β-elemonic acid is recovered in a rapid and simple manner by utilizing all the elemi acids present in the elemi acid concentrate. In order to recover an elemi acid concentrate, the gum elemi is made into a slurry in an alcoholic solvent, e.g. methanol, and the residue filtered off. The clear solution is thoroughly stirred with a basic ion exchanger. The ion exchange resin is then filtered off, washed with an alcoholic solvent, and eluted with methanolic acetic acid solution and the eluate is evaporated.

Suitable alcoholic solvents which may be used include alkanols having 1 to 3 carbon atoms, i.e. methanol, ethanol, propanol and isopropanol. Basic ion exchangers suitable for use include cross-linked synthetic resins containing trialkylammonium groups which are especially suitable for separation of water soluble organic compounds, e.g. Dowex 1×8, Amberlite IRA 401 and Amberlyst A 26. The methanolic acetic acid solution elutant contains 5-25% acetic acid in methanol. Other suitable elutants include 5-25% acetic acid in ethanol, 5-25% acetic acid in propanol and 5-25% acetic acid in isopropanol.

In the residue are contained the elemi acids β-elemonic acid, $\Delta^7\alpha$-elemolic acid and $\Delta^8\alpha$-elemolic acid. The advantage of this process lies in the substantially quantitative extraction yield with a content of 90-95% elemi acids in the concentrate. A further advantage is the reusability of the ion exchanger after regeneration and separation of about 20% insoluble by-products, especially amyrines. The isomerization of the $\Delta^7\alpha$-elemolic acid contained in the elemi acid concentrate to $\Delta^8\alpha$-elemolic acid is carried out, without previous separation of the elemi acids, in a chlorinated hydrocarbon using a mineral acid.

Suitable chlorinated hydrocarbons include chloroform, dichloromethane, 1,1-dichloroethane 1,2 dichloroethane and the like. Mineral acids which may be used include hydrochloric acid, hydrobromic acid and sulfuric acid. The isomerization may be conducted at a temperature of from 0° to 40° C., e.g. at room temperature, for from 2 to 8 hours. The chlorinated hydrocarbon phase is separated, washed with water and neutralized with an alkaline solution such as a saturated sodium hydrogen carbonate solution, a 10% sodium carbonate solution, a 10% potassium carbonate solution or the like. The residue may be recrystallized from an alkanol containing 1-3 atoms, e.g. methanol.

The oxidation of $\Delta^8\alpha$-elemolic acid to $\beta$-elemonic acid is carried out on the crude mixture by an Oppenauer reaction with aluminum isopropoxide in cyclohexanone. The final purification takes place by simple column chromatography on silica gel. The yields of $\beta$-elemonic acid from Manila gum elemi can thus be substantially improved.

The Oppenauer reaction is well known and disclosed in Org. Reactions, 6, 207 (1951). The $\Delta^8\alpha$-elemolic acid may also be oxidized by pyridinium chromate. Typically, the oxidation is carried out at a temperature of 0° to 100° C. for from 5 to 12 hours. Following the oxidation, the reaction mixture may be further treated and purified as is well known in the art, for example by separating the crude elemonic acid by extraction with dichloromethane, evaporating the solvent and treating the residue with n-hexane. Final purification takes place by column chromatography by elution with a mixture of dichloromethane and methanol followed by evaporation and final recrystallization from acetone.

The superiority of the new process is made clear by the following scheme for the recovery of $\beta$-elemonic acid.

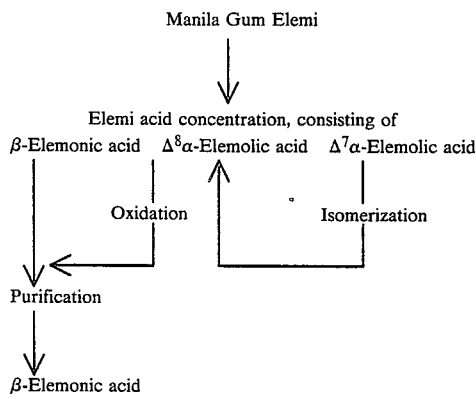

The $\beta$-elemonic acid can be worked up to pharmaceutical preparations by mixing a predetermined amount of active substance into a composition with inorganic or organic, solid or fluid, pharmaceutically acceptable substances. The resulting pharmaceutical preparations can be administered either enterally or parenterally.

There can thus be used tablets or gelatine capsules which contain the active ingredient together with diluents, e.g. lactose, dextrose, sucrose, mannitol, sorbitol, cellulose and/or glycerine, and lubricants, e.g. silica, talc, stearic acid or salts thereof, such as magnesium or calcium stearate and/or polyethylene glycol. Tablets likewise contain binders, e.g. magnesium or aluminum silicate, starch, such as corn, wheat or rice starch, gelatine, methyl cellulose, sodium carboxylmethyl cellulose and/or polyvinyl pyrrolidone and, if desired, disintegrants, e.g. starches, agar, alginic acid or a salt thereof such as sodium alginate, and/or effervescent agents or adsorbants, dyes, flavorings and sweetners. The $\beta$-elemonic acid can be used further in the form of injectable, e.g. intravenously administrable, preparations or infusion solutions. Such solutions are preferably isotonic aqueous solutions or suspensions, and they can be prepared before use, e.g. from lyophilized preparations which contain the active substance together with a carrier. The pharmaceutical preparations can be manufactured in a manner known per se, e.g. by means of conventional mixing, granulating, dragee-forming, solution or lyophilization processes.

The dosages of the pharmaceutical preparations to be administered in any given case contain 10-500 mg of $\beta$-elemonic acid, preferably 10-200 mg, expecially 50-100 mg per dose, which can be administered once per day or more often.

The pharmaceutical effectiveness of $\beta$-elemonic acid was determined in the following tests.

1. The antiphlogistic effectiveness was determined by the rat paw edema test of Hillebrecht (J. Hillebrecht, Arzneim, Forsch. 1954, Vol. 4, p. 607). In this test, rats weighing from 120 g-160 g were given a subplantar dose of carrageenin (0.5% in 0.9% NaCl solution) in an amount of 0.1 ml of solution per paw, using one hind paw of each rat, to produce edema. After administration of the test substance, which as a rule should not exceed a volume of 10 ml/kg body weight, the volume of the paw was determined in an overflow device. After three hours the final value was determined. For each dosage level the experiment was performed with five test and five control animals of one sex and repeated with the same number of animals of the opposite sex. The result is expressed as the percentage inhibition of edema as compared with the control group.

TABLE 1

| | $\beta$-Elemonic Acid | | |
|---|---|---|---|
| Dose (mg/kg p.o.) | 1 | 10 | 100 |
| Inhibiting effect (%) | −7 | −21 | −33 | p.o. = per os, i.e. by mouth

A comparison test with phenylbutazone, a well known inflammation-inhibiting substance, gave a reduction of edema only at a fairly high dosage level in the carrageenin paw edema test in rats according to Hillebrecht.

TABLE 2

| | Phenylbutazone | |
|---|---|---|
| Dose (mg/kg p.o.) | 10 | 100 |
| Inhibition effect (%) | ±0 | −41 |

2. As a further experiment for testing the antiphlogistic effectiveness there was used rat paw edema induced by means of cobra venom factor (CVF). Since CVF produces inflammation by way of activation of the complementary system, inhibiting substances could open up a new kind of working principle for application in inflammatory illnesses.

Edema was provoked by subplantar injection of CVF (10 units in 1 ml NaCl solution 0.9%) in an amount of 0.1 ml of solution per paw, into one hind paw of each of a number of rats weighing from 120-160 g. After administration of the test substance in a volume of 10 ml/kg body weight the volume of the paw was determined in an overflow device. After three hours the final value was determined. For each dose the test was carried out with five test and five control animals of one sex, and repeated with the same number of animals of the opposite sex. The result was expressed as percentage inhibition of the edema compared with the control group. The following values were obtained:

TABLE 3

| | β-Elemonic Acid | | |
|---|---|---|---|
| Dose (mg/kg p.o.) | 1 | 10 | 100 |
| Inhibition effect (%) | −24 | −32 | −49 |

A comparison test with phenylbutazone gave weaker inhibition values in this test, so that advantages can be seen for the β-elemonic acid.

TABLE 4

| | Phenylbutazone | | |
|---|---|---|---|
| Dose (mg/kg p.o.) | 1 | 10 | 100 |
| Inhibition effect (%) | +10 | −28 | −34 |

3. The adjuvant arthritis test of C. M. Pearson, Proc. Soc. Exp. Biol. 91, 95-101 (1956) was carried out as a further relevant animal experiment for the examination of anti-rheumatic substances.

Ten Wistar rats weighing from 120-150 g were used for each dose. The same number of animals served as a control. Arthritis was induced with 0.5 ml Freud's adjuvant, by subplantar injection. The test lasted 17 days. At the beginning of the test the paw volume of the non-injected hind paw was determined and this was used as a starting value. Further volume measurements were carried out on the 14th and 17th days of the test. For the result the difference between the starting and finishing volumes of the paw, both of the test group and of the control group, was obtained and the inhibition expressed as a percentage. With daily administration from the time of induction of arthritis onwards (prophylactic application) the following inhibition values (%) were obtained:

TABLE 5

| | β-Elemonic acid | | | Phenylbutazone | | |
|---|---|---|---|---|---|---|
| Dose (mg/kg p.o.) | 1 | 10 | 100 | 10 | 31,6 | 82,5 |
| 14th day p.i. | −55 | −62 | −165 | −42 | −57 | −58 |
| 17th day p.i. | −38 | −47 | −92 | −31 | −51 | −43 | p.i. = post injection

Even in therapeutic application beginning ten days after the induction of arthritis, pronounced inhibition values (%) of β-elemonic acid were recorded.

TABLE 6

| | β-Elemonic acid | | |
|---|---|---|---|
| Dose (mg/kg p.o.) | 1 | 10 | 100 |
| 14th day p.i. | +36 | −13 | −38 |
| 17th day p.i. | −31 | −42 | −81 |

The most frequent side effect in known anti-rheumatics is poor gastrointestinal tolerance with ulcer induction. For this reason β-elemonic acid was examined for the induction of ulcers. The determination of ulcer formation was made according to W. J. R. Whittle, Brit. J. Pharmacology, 1975, Vol. 55, pp. 242-243; L. Mariani, Europ. J. Toxicol. Eviron., 1975, Vol. 8, pp. 335-39; and R. Menguy and L. Desbaillets, Proc. Soc. Bio., Vol. 125, p. 1108. In the tests, for each dose and control ten male Wistar rats (120-150 g, kept fasting for 16 hours) were used. The provocation of bleeding stomach ulcer took place by oral application of the active ingredient. The animals were sacrificed after 3.5 hours, the stomach removed, opened along the larger curvature and stretched on a foam polystyrene plate. The median ulcer factor of the test group and the control group was determined. The following effects were observed with a single administration following previous sensitization of the stomach mucosa by a three-day carbohydrate diet:

TABLE 7

| | β-Elemonic acid | | Phenylbutazone | |
|---|---|---|---|---|
| Dose (mg/kg p.o.) | 10 | 100 | 316 | 200 |
| Effect | 0 | 0 | 0 | +++ |

0 = no ulcer induction
+ = moderate ulcer induction
++ = strong ulcer induction
+++ = very strong ulcer induction Determination of toxicity of β-elemonic acid was carried out on the mouse and the rat. Acute peroral toxicity in the mouse: 4.640 mg/kg. Comparison phenylbutazone, oral, mouse: $LD_{50}$ 465 mg/kg.

In a dose-range study on rats there were no occurrences of aggravating side-effects following daily application for 14 days with dosages of 681.0 and 1,000.0 mg/kg body weight.

β-Elemonic acid was compared with prednisolone for determining side-effects. Known antiphlogistic substances can cause undesired side-effects, some of which arise even at therapeutic doses. For this reason a comparative investigation of β-elemonic acid with prednisolone was undertaken (H. J. Lee, M. R. I. Soliman in Science 215 989-991, 1982). Carried out on young rats, the duration of application was 8 days. β-Elemonic acid was administered orally up to a dosage of 316 mg/kg body weight, and prednisolone intramuscularly up to a dosage of 5 mg/kg body weight. The following individual results were obtained:

TABLE 8

| | β-Elemonic acid | | Prednisolone | |
|---|---|---|---|---|
| Dose (mg/kg) | 100 | 316 | 2,5 | 5 |
| Body weight development | (−) | (−) | − | − |
| Liver weights | 0 | 0 | 0 | 0 |
| Thymus weight | 0 | (−) | − − − | − − − |
| Blood picture | | | | |
| Lymphocytes | 0 | 0 | (−) | − |
| Leucocytes | 0 | 0 | 0 | − |

0 = no effect
(−) = weak inhibition
− = definite inhibition
− − − = very strong inhibition As early as the termination of the adjuvant arthritis in 17-day administration of substance (propylactic application) it was determined that the adrenal gland weights after β-elemonic acid administration lie inside the normal limits.

An assessment of the effectiveness of elemonic acid was compared with known substances. A quantitative assessment of β-elemonic acid in comparison with known antiphlogistic substances was made possible by determining the therapeutic ranges, i.e. by the safety with which an active ingredient can be used. For comparison, indomethacin served as a strongly active antiphlogistic, as well as phenylbutazone as a weakly active one, an appraisal which arises from their respective $ED_{50}$ values in the arthritis test. The therapeutic range is given (1) by the ratio between the $LD_{50}$ and the $ED_{30}$ in the CVF paw oedema and (2) by the ratio between the dose threshold value of stomach intolerance and the $ED_{50}$ in the arthritis model. The $ED_{30}$ and the $ED_{50}$ values were determined with the aid of a regression line:

TABLE 9

Dose-activity ratio and therapeutic range

| | $\beta$-Elemonic-acid | Phenyl-butazone | Indo-methacin |
|---|---|---|---|
| 1. $ED_{30}$ (mg/kg p.o.) CVF edema | 3.98 | 37.66 | 4.58 |
| 2. $ED_{50}$ (mg/kg p.o.) Adjuvant arthritis prophyl. | 4.64 | 47.50 | 0.26 |
| 3. $LD_{50}$ (mg/kg p.o.) Mouse | 4640.00 | 465.00 | 40.00 |
| 4. Threshold dose (mg/kg p.o.) Acute stomach mucous tolerability | 316.00 | 25.00 | 5.62 |
| 5. Therapeutic index 1 (3./1.) | 1165.00 | 12.35 | 8.73 |
| 6. Therapeutic index 2 (4./1.) | 68.00 | 0.53 | 21.62 |

Therapeutic indices 1 and 2 as measures of the therapeutic range, are each several times higher with $\beta$-elemonic acid than with comparison substances. Thus $\beta$-elemonic acid shows, in addition to its good antiphlogistic activity, the advantages of improved safety in its application compared with known antiphlogistics.

EXAMPLE 1

$\beta$-Elemonic acid (a) Elemi acid concentrate: 1 kg of gum elemi was stirred in 10 l methanol and filtered off from undissolved material. The clear solution was treated with 1 kg of a strongly basic ion exchanger (OH$^-$-form, washed with methanol) and stirred for three hours. The exchange resin was filtered off and washed with methanol until no more by-products could be detected in the filtrate. The detection was performed with TLC (thin layer chromatography) or HPLC (high pressure liquid chromatography). Elution was performed with a 10% methanolic acetic acid solution, to detach the elemi acids from the ion exchanger. Further pure methanol was used for elution until no elemi acid could be detected in the run-off. The anion exchanger used was Amberlyst A 26. On evaporation of the eluate there was obtained an elemi acid concentrate, consisting essentially of:

$\beta$-Elemonic acid—about 15-20%
$\Delta^8\alpha$-Elemolic acid—about 50-60%
$\Delta^7\alpha$-Elemolic acid—about 20-30%
Yield based on Manila gum elemi: 200-250 g
Elemi acid content: 90-95%

(b) Isomerization of $\Delta^7\alpha$-elemolic acid to $\Delta^8\alpha$-elemolic acid in the crude elemi acid mixture.

1 kg elemi acid mixture (prepared according to method (a)) was dissolved in 6 l of chloroform, treated with one l 36% hydrochloric acid and stirred at room temperature for 5 hours. The chloroform phase was separated, washed neutral with water and a saturated sodium hydrogen carbonate solution, dried over anhydrous sodium sulfate and evaporated. The residue obtained was recrystallized from 3 l methanol.

Yield (based on concentrate used): 60-70%.
Composition: 10-15% $\beta$-elemonic acid; 80-85% $\Delta^8\alpha$-elemolic acid; <1% $\Delta^7\alpha$-elemolic acid; about 5% by-products.

(c) Oxidation of the $\Delta^8\alpha$-elemolic acid in the elemi acid mixture.

20 g elemi acid mixture (prepared according to method (b)), 122 g aluminum isopropoxide and 1500 ml cyclohexanone were stirred in a 4 l round flask having an internal thermometer, stirrer and fitted distillation bridge at a 60° C. bath temperature until a clear solution appeared. Then the bath temperature was raised to 100° C. and the mixture stirred for a further 5-6 hours, with application of a week vacuum of 200 mbar, to remove cyclohexanol formed. The reaction was monitored by means of TLC or HPLC. After cooling to room temperature the mixture was transferred to a 5 l glass beaker. About one l crushed ice and 200 ml 36% hydrochloric acid were added with stirring. One l water and one l dichloromethane were then added and the mixture stirred for a further 5-10 minutes. The organic phase was separated in a separating funnel and stirred with 2 l of a saturated sodium hydrogen carbonate solution to remove excess acid. The organic phase was washed neutral with water and dried over anhydrous sodium sulfate.

The dichloromethane was distilled off at a bath temperature of 50° C. on a rotary evaporator and the excess cyclohexanone removed at 100° C. with a water jet pump vacuum. The residue was treated with the same volume of n-hexane and stirred for 3-6 hours. The white solid was filtered off, washed with n-hexane and dried in the vacuum drying cabinet. Yield of crude $\beta$-elemonic acid (based on elemi concentrate used): 53-60%.

(d) Final purification of the $\beta$-elemonic acid.

A chromatographic column (20 cm$\phi$, length 50 cm) was filed with 4 kg silica gel Si 60, 0.063-02 mm particle size, and thoroughly moistened with dichloromethane. 400 g crude $\beta$-elemonic acid (prepared according to method (c)) was dissolved hot in 2 l dichloromethane and, after cooling, fed to the column. Elution was performed with a mixture of dicloromethane/methanol 100:1. About 30 l eluate was taken as a first run. The $\beta$-elemonic acid was obtained pure from the main run (50-70 l eluate) by evaporation followed by recrystallization from acetone. The progress of the chromatography was monitored by means of TLC or HPLC. The yield of pure $\beta$-elemonic acid was 240-300 g corresponding to 60-75%.

EXAMPLE 2

Preparation of Tablets

Composition:
$\beta$-Elemonic acid: 50.0 mg
Lactose: 38.0 mg
Corn starch: 50.0 mg
Polyvinyl pyrrolidone: 5.0 mg
Colloidal silicon dioxide: 2.0 mg
Magnesium stearate: 1.0 mg
Sodium carboxymethyl starch: 4.0 mg The elemonic acid, lactose and corn starch were granulated with an aqueous solution of the polyvinyl pyyrolidone. The dried granulate was mixed with the magnesium stearate, colloidal silicon dioxide and sodium carboxymethyl starch and compressed to tablets with a diameter of 8 mm.

EXAMPLE 3

Preparation of Hard Gelatine Capsules

Composition:

β-Elemonic acid: 80.0 mg
Lactose: 50.0 mg
Corn starch: 70.0 mg
Magnesium stearate: 1.0 mg
Colloidal silicon dioxide: 2.0 mg The active ingredient was mixed with the adjuvants and filled into hard gelatine capsules of size 3.

What is claimed is:

1. A process for the production of β-elemonic acid from an alcoholic solution of gum elemi which comprises recovering a crude mixture of elemi acids consisting essentially of β-elemonic acid, $\Delta^7\alpha$-elemolic acid and $\Delta^8\alpha$-elemolic acid, isomerizing the $\Delta^7\alpha$-elemolic acid to $\Delta^8\alpha$-elemonic acid in a chlorinated hydrocarbon in the presence of a mineral acid, oxidizing the $\Delta^8\alpha$-elemolic of the crude acid mixture to yield additional β-elemonic acid, and separating the total resulting β-elemonic acid from said crude acid mixture.

2. The process according to claim 1, wherein the separated β-elemonic acid is purified by chromatography on silica gel.

3. A process which comprises administering to a human or animal suffering from inflammatory conditions an effective amount of a preparation containing β-elemonic acid combined with a pharmaceutically acceptable carrier.

4. The process of claim 3, wherein the β-elemonic acid contained in the preparation is prepared by the process of claim 1.

* * * * *